United States Patent [19]

Dieguez et al.

[11] Patent Number: 5,382,422
[45] Date of Patent: Jan. 17, 1995

[54] METHOD AND APPARATUS FOR FORMATION AND DELIVERY OF INSECT ATTRACTANT BASED ON CARBON DIOXIDE

[75] Inventors: Jose M. Dieguez, St-Bruno; Robert G. H. Lee, Montreal, both of Canada

[73] Assignees: Canadian Liquid Air Ltd.,; Air Liquide Canada Ltee, Montreal, Canada

[21] Appl. No.: 769,245

[22] Filed: Oct. 1, 1991

[30] Foreign Application Priority Data

Oct. 4, 1990 [CA] Canada ............................ 2026945

[51] Int. Cl.⁶ .................. A01N 25/06; A01N 31/02
[52] U.S. Cl. ............................ 424/45; 424/84; 424/405; 424/700; 43/111; 514/675; 514/724
[58] Field of Search ............ 424/84, 405, 700, 45; 252/373; 137/572; 436/11, 68; 62/48.1, 50.2; 43/111

[56] References Cited

U.S. PATENT DOCUMENTS

| | | | |
|---|---|---|---|
| 831,941 | 9/1906 | Erlinger | 424/700 |
| 1,775,703 | 9/1930 | Stokes | 424/700 |
| 4,127,008 | 11/1978 | Tyree, Jr. | 62/62 |
| 4,202,180 | 5/1980 | Cox | 62/50 |
| 4,281,171 | 7/1981 | Sims | 560/124 |
| 4,770,780 | 9/1988 | Moses | 210/634 |
| 5,108,799 | 4/1992 | Hoy et al. | 427/422 |
| 5,113,905 | 5/1992 | Pruitt et al. | 137/571 |

OTHER PUBLICATIONS

Holscher et al., Ann. Entomol. Soc. Am. 73:288–292 (1980) Electro Physiological Responses of Threetick Species to Carbon Dioxide in The Laboratory and Field.
Griffiths et al. Acarology III vol. 2, 1984, p. 1067.
*Anesthesia* by James Gwathmey; Macmillan, 1924 pp. 152, 153, 158–163 224, 228.
Garcia: Ann. Ent. Soc. Amer. 55:605:1962 Carbon Dioxide as a Attractant for Certain Ticks.
Vale, G. A. and Hall D. R. 103:175867k 1985 p. 454 Chem. Abst. Role of 1-octen-3-ol, acetoned $CO_2$u Attraction of Tsetse flies.

*Primary Examiner*—D. Gabrielle Phelan
*Assistant Examiner*—Neil Levy
*Attorney, Agent, or Firm*—Oblon, Spivak, McClelland, Maier & Neustadt

[57] ABSTRACT

A method and apparatus to prepare and deliver a gas mixture of constant composition of liquid chemical compounds soluble in liquid carbon dioxide to be used as an enhanced attractant for biting insects. The mixtures can be prepared in high pressure vessels where carbon dioxide remains liquified under its own vapor pressure or in low pressure vessels where carbon dioxide is kept liquid, at low pressure, by cooling it with a refrigeration unit. Direct vaporization of the liquid mixture from the vessels results in a gas mixture of constant composition. This mixture is to be delivered in a continuous or pulsed flow to an insect trap. These baited insect traps are an ecological alternative to chemical insecticide methods of insect control currently in use.

2 Claims, 2 Drawing Sheets

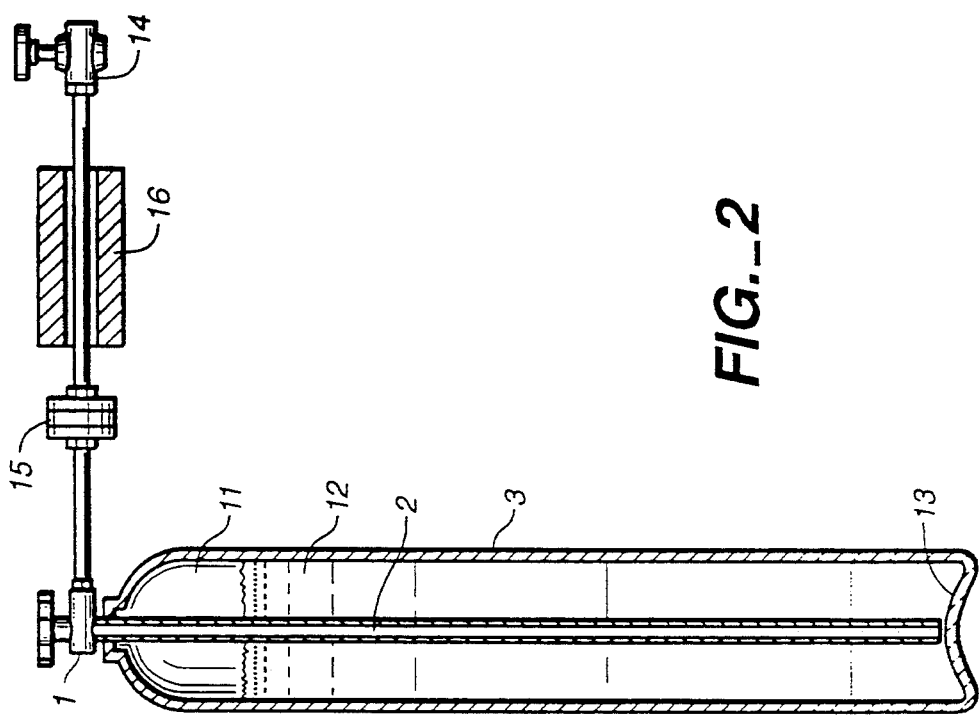
FIG._2
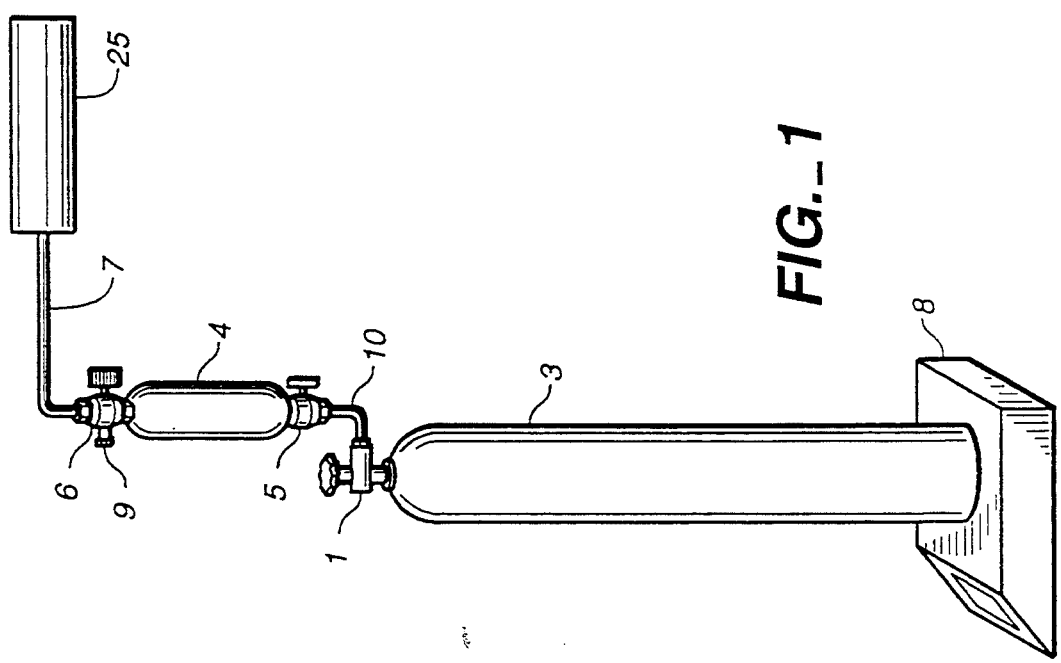
FIG._1

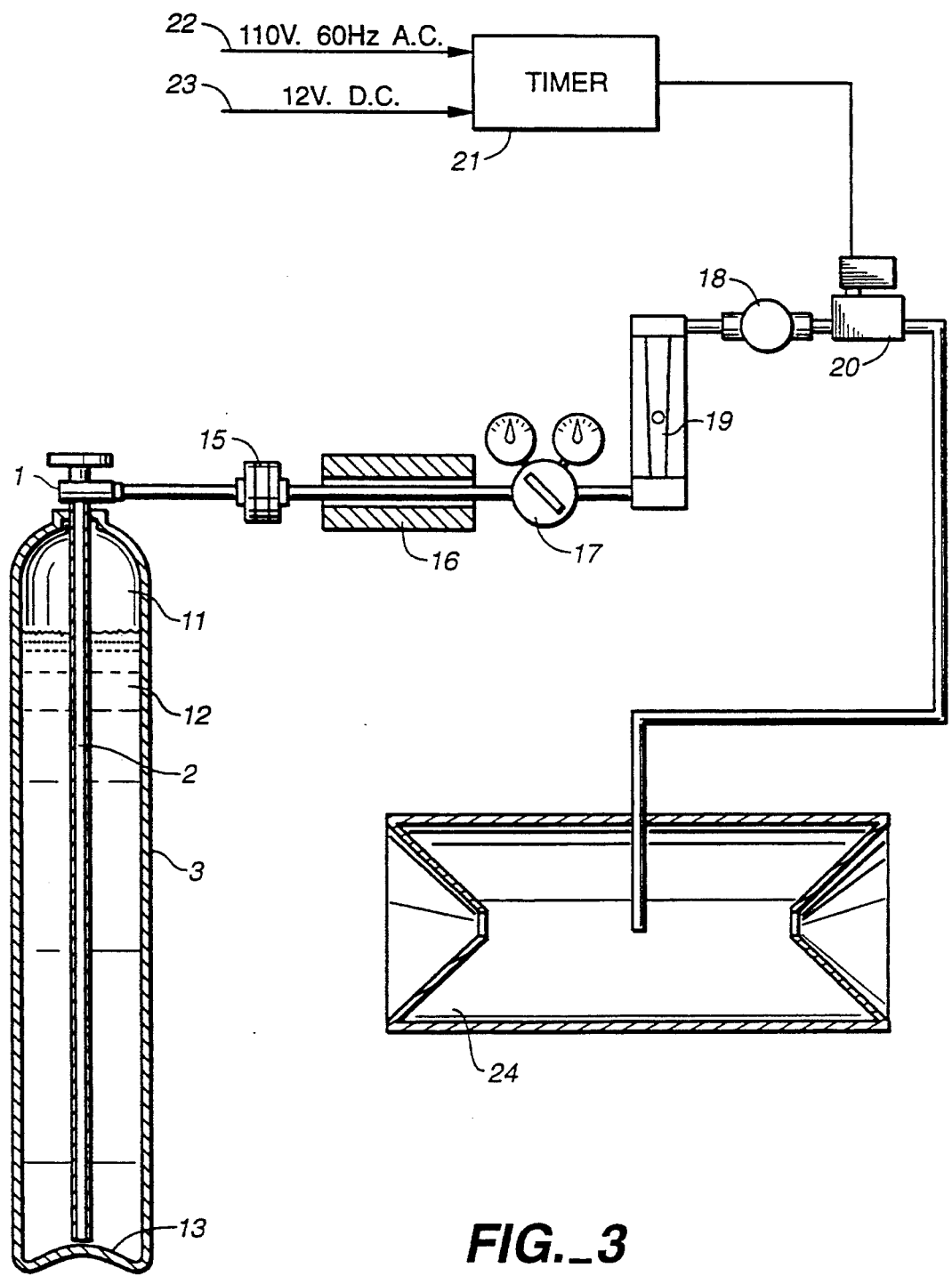
FIG._3

METHOD AND APPARATUS FOR FORMATION AND DELIVERY OF INSECT ATTRACTANT BASED ON CARBON DIOXIDE

BACKGROUND OF THE INVENTION

1. Field of the Invention

This invention relates to a method and apparatus for preparing a liquid mixture of liquid carbon dioxide and a liquid chemical soluble in liquid carbon dioxide; to a method and apparatus for producing a flow of such liquid mixture; and to a method and apparatus for producing a flow of carbon dioxide gas containing vapor of such liquid chemical.

2. Discussion of the Background

Carbon dioxide is used as an attracting agent for removal trapping or destructive sampling of biting insects. The use of carbon dioxide together with certain other chemical compounds, for example, acetone or octenol, produces a synergistic effect greatly increasing the trapping results for certain insects.

Carbon dioxide is available as a liquified gas under its own vapor pressure of 5.7 MPa at 20° C. in standard high pressure vessels containing 9 to 23 kg of carbon dioxide. Liquid carbon dioxide is also available from low pressure, insulated bulk vessels, where the pressure is kept low by maintaining the temperature at a suitable low level with a mechanical refrigeration unit. Low pressure vessels are available in capacities of 2,720 kg, 3,630 kg, 5,440 kg, 11,800 kg, 21,800 kg and 28,100 kg.

Liquid carbon dioxide is a very good solvent for many chemical compounds. This property is used to extract and recover chemical products from natural and synthetic mixtures. Acetone, for example, is completely soluble in liquid carbon dioxide. The solubility of octenol in liquid carbon dioxide is about 5% by weight.

Homogeneous mixtures of acetone or octenol in liquid carbon dioxide can be prepared in high or low pressure vessels provided the concentrations are kept below the solubility limits.

Currently, mixtures of acetone or octenol in carbon dioxide are prepared dynamically by metering a flow of gaseous carbon dioxide from a standard vessel and mixing it with acetone or octenol vapor obtained by evaporation from a wick in a liquid reservoir. The acetone or octenol concentration depends on the reservoir temperature, state of the wick and the stability of the carbon dioxide flow.

Homogeneous gas mixtures of acetone or octenol in gaseous carbon dioxide can be prepared in a vessel provided that the final pressure is below the vapor pressure of the carbon dioxide or the acetone or octenol, at the minimum exposed temperature of the vessel. This is to eliminate condensation of any component of the mixture. The final pressures are so low that the quantity of the mixture available from the vessels is very small.

Liquid mixtures of acetone or octenol in carbon dioxide would provide an easy method to store and to deliver the required quantities of homogeneous gas mixture, by using liquid withdrawal and followed by vaporization.

SUMMARY OF THE INVENTION

The present invention seeks to provide a method and apparatus for preparing and delivering a liquid mixture of liquid carbon dioxide and a liquid chemical soluble in the liquid carbon dioxide which permits preparation of bulk quantities of the liquid mixture; and in particular permits preparation of bulk quantities of a homogeneous liquid mixture having a known content of the chemical and the carbon dioxide which homogeneous liquid mixture is a source of carbon dioxide gas containing a vapor of the liquid chemical.

In accordance with one aspect of the invention there is provided a method of preparing a liquid mixture of known composition of liquid carbon dioxide and a liquid chemical soluble in liquid carbon dioxide comprising: providing an evacuated first vessel of known weight, for housing liquid carbon dioxide, providing a second vessel containing a predetermined weight of the liquid chemical soluble in carbon dioxide, flowing said predetermined weight of said chemical from said second vessel into said evacuated first vessel and flowing liquid carbon dioxide through said second vessel into said first vessel until a predetermined weight of liquid carbon dioxide is contained with said chemical in said first vessel.

in accordance with a particular aspect of the invention the aforementioned method is exploited to provide a flow of the liquid mixture, in which a gaseous head space under pressure is maintained above the liquid mixture in the first vessel. An out-flow conduit means is connected to the first vessel and the pressure of the gaseous head space forces liquid mixture from the first vessel into the out-flow conduit means.

In accordance with still another aspect the latter method is exploited to provide a flow of a mixture of carbon dioxide gas and vapor of the liquid chemical by vaporizing the liquid mixture in the out-flow conduit means. The vaporized liquid mixture may be delivered by the out-flow conduit means to a desired site, for example, to one or more insect traps, when the vaporized mixture is an insect attractant.

In accordance with another aspect of the invention there is provided an apparatus for preparing a liquid mixture of known composition of liquid carbon dioxide and a liquid chemical soluble in liquid carbon dioxide comprising: a first vessel having a port for flow of liquid, means for monitoring the weight of the first vessel, a second vessel having first and second valve-controlled flow ports, flow conduit means adapted to connect said port of said first vessel and said first valve-controlled flow port of said second vessel with said second vessel disposed above said first vessel, said second valve-controlled flow port being adapted to be connected to a source of liquid carbon dioxide.

In still another aspect of the invention there is provided an apparatus for delivering the liquid mixture.

BRIEF DESCRIPTION OF THE DRAWINGS

The invention is illustrated in particular and preferred embodiments by reference to the accompanying drawings in which:

FIG. 1 illustrates schematically an apparatus for preparing a liquid mixture in accordance with the invention;

FIG. 2 illustrates schematically an apparatus of the invention for delivering a continuous supply of vaporized liquid mixture; and FIG. 3 illustrates schematically an apparatus of the invention for delivering a pulsed supply of vaporized liquid mixture to an insect trap.

DETAILED DESCRIPTION OF THE EMBODIMENTS

With further reference to FIG. 1 a vessel 3 where the liquid mixture is to be prepared is provided with a syphon valve 1. Syphon valve 1 has an elongate tube 2 permanently mounted in its upper end and extending to the floor of vessel 3.

The acetone or octenol to be added to the liquid carbon dioxide, is introduced by the use of intermediate vessel 4 which is small in volume (as compared to vessel 3) because the acetone or octenol is to be filled by weight. The working pressure of the intermediate vessel 4 should be equal to or higher than that of vessel 3 where the liquid mixture is to be prepared. Intermediate vessel 4 is equipped with valves 5 and 6. This allows the intermediate vessel 4 to be placed between the liquid mixture vessel 3 and a liquid carbon dioxide supply line to a tank 25 of liquid carbon dioxide.

The vessel 3 where the liquid mixture is to be prepared is provided with a facility to determine its contents by weight. In the case of a high pressure vessel 3, this can be achieved by placing the vessel 3 on a scale 8. Large bulk vessels can be weighed directly with strain gauges or indirectly by weighing the delivery vessels, before and after delivery. With suitable calibration, the liquid level in a vessel 3 can also be converted into a weight basis.

An example will show the method, procedure and equipment to prepare a mixture in liquid carbon dioxide.

A mixture of 5% by weight of acetone in liquid carbon dioxide is to be prepared in a high pressure vessel 3 of 23 kg capacity.

The quantity of acetone necessary for this mixture is $0.05 \times 23 = 1.15$ kg. Acetone has a specific gravity at 20° C., of 0.791. Therefore 1.15 kg represents 1.454 $dm^3$ of acetone.

A standard 2.250 $dm^3$ stainless steel sampling vessel (working pressure 12.5 MPa) with two valves is a suitable intermediate vessel 4 to prepare this mixture. One valve 5 is suitably a ball valve to allow the introduction of the acetone with a suitable funnel and a second valve 6 is suitably a non-rotating stem valve equipped with a rupture disc 9 rated at a nominal bursting pressure of 13.1 MPa.

After purging the intermediate vessel 4 with gaseous carbon dioxide, this carbon dioxide filled vessel 4 at atmospheric pressure is weighed. With a suitable funnel, a measured volume of 1.454 $dm^3$ of acetone is introduced in vessel 4. It will be understood that at this stage intermediate vessel 4 is not connected between vessel 3 and supply line 7 and for introduction of the acetone is inverted for filling via valve 5 with use of a suitable funnel. The vessel 4 is weighed again. The amount of acetone in vessel 4 should be very close to 1.15 kg.

A standard high pressure 23 kg vessel 3 with a syphon valve 1, is placed under vacuum. The cylinder 3 is weighed under vacuum on scale 8. The cylinder 3 should preferably remain on the scale 8.

As shown in FIG. 1, the intermediate vessel 4 is connected by valve 5 to the evacuated carbon dioxide vessel 3 with a short 90° connection 10, to keep the intermediate vessel 4 in a vertical position. This is to facilitate the introduction of the acetone in the intermediate vessel 4 into the evacuated carbon dioxide vessel 3 by the combined action of gravity and the vacuum in vessel 3.

The intermediate vessel 4 is connected by valve 6 to the liquid carbon dioxide supply line 7. The line 7 may suitably be provided with pressure gauges (not shown) and a vacuum system (not shown) to vacuum and purge the supply line 7 as required.

After opening syphon valve 1 of the evacuated carbon dioxide vessel 3, the valve 5 of the intermediate vessel 4 closer to the evacuated carbon dioxide vessel 3 is opened. By the joint action of gravity and vacuum, the acetone is transferred from the intermediate vessel 4 into the evacuated carbon dioxide vessel 3.

After opening the second valve 6 of the intermediate vessel 4, liquid carbon dioxide is allowed to flow into the evacuated carbon dioxide vessel 3 via intermediate vessel 4. The liquid carbon dioxide introduction should be stopped when the total content in the vessel 3 is 23 kg. The actual amount of liquid carbon dioxide introduced can be calculated by the difference between the total weight and the weight of acetone. The final concentration of this mixture can be calculated from these values.

The liquid carbon dioxide should preferably be introduced at very high flows, suitably at a flow rate of more than 0.5 kg/min., to induce turbulence in the evacuated liquid carbon dioxide vessel 3. This is to accelerate the mixing of the acetone and the liquid carbon dioxide.

The evacuated carbon dioxide vessel 3, which is now filled with the liquid mixture of acetone and liquid carbon dioxide, can then be disconnected from the filling system. As illustrated in FIG. 2, the contents of this vessel 3 containing the mixture are about 90% by weight liquid mixture 12 to 10% gas 11.

At constant temperature, the pressure of the liquid mixture in the vessel 3 remains the same while the vessel 3 still contains the liquid mixture 12. When the liquid mixture 12 is completely exhausted and vessel 3 contains only the gas phase 11, the vessel 3 content is about 30% by weight of the total mixture. From this moment on, the pressure starts to drop.

Generally, the vapor pressure of the chemical compounds to be dissolved in liquid carbon dioxide is lower than that of pure carbon dioxide. These chemical compounds concentrate in the liquid phase 12. The gas phase 11 is a homogeneous gas mixture, of somewhat lower concentration, of these soluble chemical compounds in carbon dioxide. The gas phase 11 can be used as an insect attractant.

The vessel 3 contains the liquid mixture 12 and by opening the syphon valve 1, a homogeneous liquid mixture is available. The pressure in the gaseous head space 11 of the vessel 3 forces the liquid 12 into the bottom 13 of the tube 2 and up through the valve 1.

A constant liquid flow can be obtained from the liquid carbon dioxide mixture 12 in vessel 3 by means of a metering device 14. If the liquid flow has to be changed, either a series of calibrated leaks or a fine metering valve 14 can be used.

A constant liquid flow can also be obtained from the liquid carbon dioxide mixture 12 in vessel 3 by means of the system shown in FIG. 3. A pressure regulator 17 is located downstream of filter 15 and heating cartridge 16 if used. The required gas flow is obtained by adjusting the low pressure of pressure regulator 17 and the use of control valve 18. The gas flow can be measured with a flowmeter 19. A solenoid valve 20 can be used to deliver a pulsed, metered flow, of the insect attractant mixture. The solenoid valve 20 can be programmed with timer 21. The timer 21 and solenoid valve 20 can be operated from a standard 110 V, 60 Hz A.C. power supply 22 or more conveniently, for field operation, from a 12 C V D.C. standard lead acid car battery 23.

The continuous or pulsed flow of the insect attractant gas mixture is fed into a series of suitable insect traps 24, such as "lard-can" trap 24, arranged in grid configurations. The insects will collect in the traps for further disposal.

Metering of the liquid flow, either with calibrated leaks, metering valves or pressure regulator systems, requires the use of fine porosity filters 15, typically 0.5 to 2 micrometers porosity. The filter 15 should be located immediately ahead of the liquid metering device 14 to reduce the possibility of malfunctioning by plugging with particulate matter potentially present in the liquid mixture.

The vaporization of the metered liquid flow requires heat. The amount of heat necessary is the latent heat of vaporization. At 20° C. and 5.7 MPa the latent heat of vaporization of carbon dioxide is 153 kJ/kg.

The heat requirement to vaporize the liquid mixture 12 depends on the total liquid flowrate. This heat requirement can be supplied, and in most cases is supplied, by the surrounding atmosphere through the vessel wall, valve, tubing, etc. If this heat input is insufficient, the liquid mixture 12 in the vessel will start to cool down. As the mixture cools, the pressure drops and therefore the flow through the metering device 14 is reduced. In such case, provision may be made for a heating cartridge 16 to supply the additional heat requirement. This heating cartridge 16 should be located between the liquid filter 15 and the liquid metering device 14.

The vessel 3 may be a high pressure vessel in which the carbon dioxide remains liquified under its own vapor pressure, or it may be a low pressure vessel in which the liquid carbon dioxide is maintained in liquid state by cooling vessel 3 with a refrigeration unit.

We claim:

1. A method of providing a flow of carbon dioxide gas containing a vapor of a liquid insect attractant soluble in liquid carbon dioxide which is selected from the group consisting of acetone and octanol, to an insect trap, which comprises:
    (a) flowing a desired amount of said liquid insect attractant soluble in liquid carbon dioxide from a second vessel into an evacuated first vessel of known weight for holding liquid carbon dioxide,
    (b) flowing said liquid carbon dioxide through said second vessel into said first vessel at a temperature and under a pressure effective to maintain flow of said liquid carbon dioxide until a desired amount of liquid carbon dioxide is contained with said liquid chemical in said first vessel with formation of a liquid mixture of liquid carbon dioxide and said insect attractant in said first vessel, and
    (c) maintaining a gaseous head space under pressure in said first vessel above the liquid mixture;
    (d) connecting said first vessel by an out-flow conduit means to the insect trap at which the carbon dioxide gas containing said vapor is desired;
    (e) allowing the pressure of gas in said head space to force the liquid mixture from said first vessel into said out-flow conduit means, and
    (f) vaporizing said liquid mixture in said out-flow conduit means
    (g) delivering the vaporized liquid mixture to said insect trap.

2. The method of claim 1, which further comprises developing a pulsed, metered flow of the vaporized liquid mixture in said out-flow conduit means.

* * * * *